United States Patent [19]

Woods et al.

[11] Patent Number: 5,021,512

[45] Date of Patent: Jun. 4, 1991

[54] THIOL/ENE COMPOSITIONS

[75] Inventors: John G. Woods, Stillorgan; John M. Rooney, South Glastonbury, Conn.

[73] Assignee: Loctite (Ireland) Ltd., Tallaght, Ireland

[21] Appl. No.: 351,310

[22] Filed: May 4, 1989

Related U.S. Application Data

[63] Continuation of Ser. No. 1,498, Jan. 5, 1987, abandoned, which is a continuation-in-part of Ser. No. 824,903, Jan. 31, 1986, Pat. No. 4,640,849, and a continuation-in-part of Ser. No. 779,737, Sep. 24, 1985, Pat. No. 4,732,956, which is a continuation-in-part of Ser. No. 667,724, Dec. 4, 1984, Pat. No. 4,543,397, which is a continuation-in-part of Ser. No. 621,419, Jun. 18, 1984, abandoned.

[30] Foreign Application Priority Data

Jan. 7, 1986 [IE] Ireland ..................... 32/86

[51] Int. Cl.$^5$ .............................................. C08F 8/34
[52] U.S. Cl. .................... 525/328.2; 522/33; 525/328.9; 525/350; 525/502; 526/301; 526/313; 526/320
[58] Field of Search ............... 526/301, 309, 313, 320; 525/350, 328.2, 328.9

[56] References Cited

U.S. PATENT DOCUMENTS

| | | | |
|---|---|---|---|
| 2,488,501 | 11/1939 | Moyle .................. | 568/646 |
| 3,327,019 | 6/1967 | Mulenbusch et al. ......... | 525/44 |
| 3,616,041 | 10/1971 | Kehr .................... | 525/350 |
| 3,661,744 | 5/1972 | Kehr et al. ............. | 428/419 |
| 3,663,625 | 5/1972 | Neville ................. | 568/632 |
| 4,272,586 | 6/1981 | Ando et al. ............. | 428/419 |
| 4,388,450 | 6/1983 | Crivello ................ | 525/502 |
| 4,486,582 | 4/1984 | Hefner, Jr. ............. | 526/301 |
| 4,543,397 | 9/1985 | Woods ................... | 525/455 |
| 4,640,849 | 2/1987 | Woods ................... | 427/54.1 |
| 4,732,956 | 3/1988 | Woods et al. ............ | 526/260 |

FOREIGN PATENT DOCUMENTS 0014785 9/1980 European Pat. Off.
1448516 9/1976 United Kingdom.

OTHER PUBLICATIONS

S. Oae, Organic Chemistry of Sulfur, 133, Plenum (1977).
Morgan et al., J. Polymer Sci: Polymer Chem. Ed., 15, 639 (1977).
Korus, R. et al., "Propagation and Termination Constants in Free Radical Polymerization" in Polymer Handbook, 2nd Edition, Brandrup and Immergut, Editors, J. Wiley & Sons, pp. II-45 through II-52, 1975.

Primary Examiner—Christopher Henderson
Attorney, Agent, or Firm—Vidas & Arrett

[57] ABSTRACT

Curable thiol/ene compositions comprise:

(1) a multifunctional styryloxy monomer having one or more of the following structures

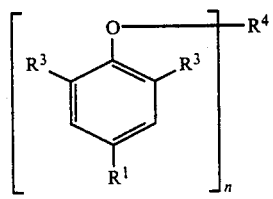

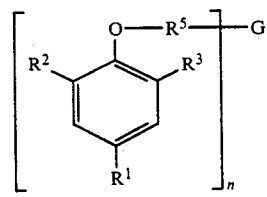

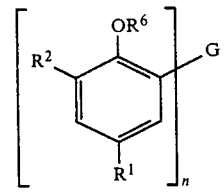

wherein
$R^1$, $R^2$ and $R^3$ are selected from vinyl ($-CH=CH_2$), 1-propenyl ($-CH=CH-CH_3$), isopropenyl $(-\underset{\underset{CH_3}{|}}{C}=CH_2)$, hydrogen, lower alkyl or alkoxy, provided that at least one of $R^1$, $R^2$ and $R^3$ must be vinyl, 1-propenyl or isopropenyl;
n is an integer $\geq 1$;
if $n=1$, then $R^4$ is a monovalent hydrocarbon radical containing one free-radically copolymerizable alkenyl or cycloalkenyl group,
if $n \geq 2$, $R^4$ is a multivalent hydrocarbon radical which may contain a maximum of one free-radically copolymerizable alkenyl or cycloalkenyl group;
$R^5$ is a divalent hydrocarbon radical; or a carbon atom which is part of a cyclic group in the radical G; or a radical of formula

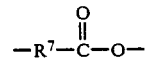

where $R^7$ is a divalent hydrocarbon radical;
if $n=1$, G is a monovalent organic or inorganic radical, free of phenolic hydroxyl groups or other groups which substantially interfere with radical polymerization, containing one free-radi- (Abstract continued on next page.)

cally copolymerizable alkenyl or cycloalkenyl group;

if $n \geq 2$, G is a multivalent organic or inorganic radical, free of phenolic hydroxyl groups or other groups which substantially interfere with radical polymerization, which may contain a maximum of one free-radically copolymerizable alkenyl or cycloalkenyl group;

$R^6$ is a lower alkyl or cycloalkyl group; or if $n=1$, $R^6$ may also be an alkenyl or cycloalkenyl group, provided that G does not contain an alkenyl or cycloalkenyl group.

(2) a multifunction thiol.

(3) a free-radical curing rate accelerator.

Novel styryloxy compounds are described which are reaction products of isoeugenol and (a) multifunctional epoxy compounds or (b) allyl glycidyl ether with or without a multifunctional polydimethylsiloxane.

10 Claims, No Drawings

THIOL/ENE COMPOSITIONS

This application is a continuation of Ser. No. 07/001,498, filed Jan. 5, 1987, now abandoned, which is a continuation-in-part of Ser. No. 824,903, filed Jan. 31, 1986, now U.S. Pat. No. 4,640,849 and a continuation-in-part of Ser. No. 779,737, filed Sept. 24, 1985, now U.S. Pat. No. 4,732,956which is a continuation-in-part of Ser. No. 667,724, filed Dec. 4, 1984, now U.S. Pat. No. 4,543,397, which is a continuation-in-part of Ser. No. 621,419 filed June 18, 1984, now abandoned.

BACKGROUND OF THE INVENTION

1. Field of the Invention

This invention relates to curable thiol/ene compositions wherein the -ene component is a multifunctional styryloxy monomer.

2. Description of Related Art

Numerous proposals have been made for curable compositions based on thiol/ene polymer systems, the essential components of which are a multifunctional alkene and a multifunctional thiol. Representative groups of thiol/ene polymers are described in U.S. Pat. No. 3,661,744 Kehr et al assigned to W. R. Grace & Co; and U.S. Pat. No. 4,008,341 Kehr, also assigned to W. R. Grace & Co; and U.S. Pat. No. 4,119,617 Hanyuda et al assigned to Showa Highpolymer Co. Ltd.

U.S. Pat. No. 4,308,367 Green et al assigned to Ciba-Geigy Corporation discloses polymerisable compositions of the thiol/ene type in which the -ene component is a compound containing in the same molecule at least one phenolic hydroxyl group and at least two groups chosen from allyl, methallyl and 1-propenyl groups. However, the phenolic hydroxyl group, being a free-radical scavenger, tends to decelerate the polymerisation reaction.

U.S. Pat. No. 4,145,479 Adams et al assigned to Armstrong Cork Company discloses a curable composition comprising at least one unsaturated polyaryoxyphosphazene, at least on aryloxy cyclotriphosphazene and a thiol crosslinking agent. Among the terminal groups suggested for the unsaturated phosphazene components are various styryloxy groups. However these compounds must have the phosphazene backbone structure, which is linked to the oxygen of the styryloxy terminal groups by a P-O- linkage, and the compounds are therefore distinct from those used in the present invention.

U.S. Pat. No. 4,543,397 Woods et al assigned to Loctite (Ireland) Limited discloses polyfunctional cationically polymerizable styryloxy compounds of the formula

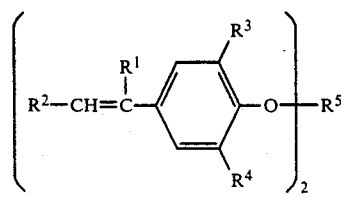

or

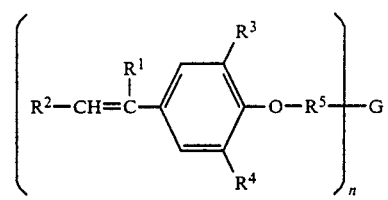

wherein $R^1$ and $R^2$ are H, or one of $R^1$ and $R^2$ are H and the other is methyl; $R^3$ and $R^4$ are H, lower alkyl, or alkoxy if $R^2$ is not methyl; $R^5$ is a divalent hydrocarbon radical; G is any multivalent organic or inorganic radical free of amino, aliphatic hydroxyl, aliphatic thiol or other groups which interfere with cationic polymerization; and n is an integer of two or more.

SUMMARY OF THE INVENTION

The present invention provides novel curable compositions comprising 1) a multifunctional styryloxy monomer having one or more of the following structures

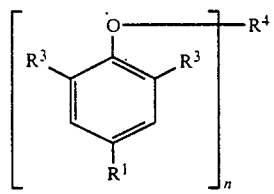

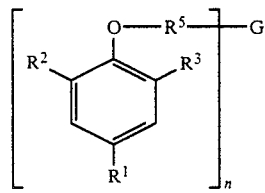

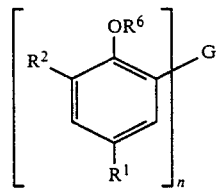

wherein:
$R^1$, $R^2$ and $R^3$ are selected from vinyl ($-CH=CH_2$), 1-propenyl($-CH=CH-CH_3$), isopropenyl

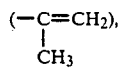

hydrogen, lower alkyl or alkoxy, provided that at least one of $R^1$, $R^2$ and $R^3$ must be vinyl, 1-propenyl or isopropenyl;

n is an integer $\geq 1$;

if n=1, then $R^4$ is a monovalent hydrocarbon radical containing one free-radically copolymerisable alkenyl or cycloalkenyl group, if n$\geq$2, $R^4$ is a multivalent hydrocarbon radical which may contain a maximum of one free-radically copolymerisable alkenyl or cycloalkenyl group;

$R^5$ is a divalent hydrocarbon radical; or a carbon atom which is part of a cyclic group in the radical G; or a radical of formula

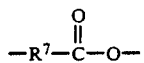

where $R^7$ is a divalent hydrocarbon radical;

if n=1, G is a monovalent organic or inorganic radical, free of phenolic hydroxyl groups or other groups which substantially interfere with radical polymerisation, containing one free-radically copolymerisable alkenyl or cycloalkenyl group;

if n≧2, G is a multivalent organic or inorganic radical, free of phenolic hydroxyl groups or other groups which substantially interfere with radical polymerisation, which may contain a maximum of one free-radically copolymerisable alkenyl or cycloalkenyl group;

$R^6$ is a lower alkyl or cycloalkyl group; or if n=1, $R^6$ may also be an alkenyl or cycloalkenyl group, provided that G does not contain an alkenyl or cycloalkenyl group.

2) a multifunctional thiol.

3) a free-radical curing rate accelerator.

The term "lower" as used herein means "having up to 10 carbon atoms", and in the preferred embodiments "having up to 5 carbon atoms".

The mole ratio of styryloxy/thiol groups is suitably from about 0.2/1 to about 5/1, preferably about 0.75/1 to about 1.5/1. $R_4$ may suitably be an alkenyl group e.g. an allylic group. When n=1, G may suitably be a substituted or unsubstituted monovalent hydrocarbon radical which may be straight or branched chain and which contains one free-radically copolymerisable alkenyl group, for example an allylic group or an allyl alkyl ether group, optionally substituted with a hydroxy group When n≧2, G may suitably be a) a polyorganosiloxane backbone, optionally substituted with styryloxy groups of the kind defined within the square brackets above, b) an n-valent hydrocarbon radical, straight or branched chain.

c) a urethane group d) an ester group e) an isocyanurate group f) an acetal group.

The invention also provides novel multifunctional styryloxy monomers including reaction products of isoeugenol and (a) multifunctional epoxy compounds or (b) allyl glycidyl ether with or without a multifunctional polydimethylsiloxane.

The multifunctional epoxy compounds are generally compounds of known type which are at least difunctional and include epoxides formed by reaction of epichlorohydrin with bisphenols or phenol formaldehyde resins (e.g. Novolac resins) or cycloalphatic epoxy compounds having at least two terminal epoxy alicyclic groups, more particularly two epoxycyclohexyl groups, such as 3,4-epoxycyclohexylmethyl-3,4-epoxycyclohexane carboxylate.

The multifunctional polydimethylsiloxanes are generally of the formula

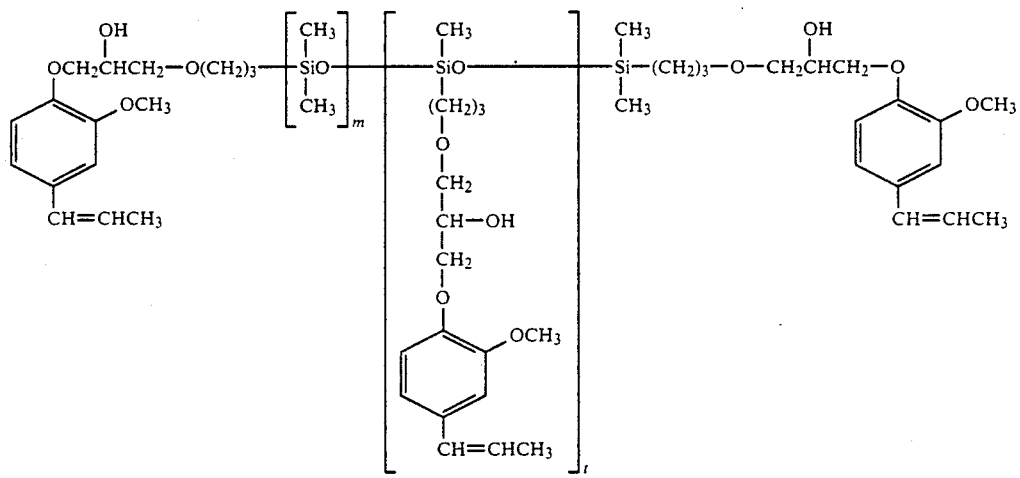

wherein t is zero or an integer, preferably less than 50, particularly less than 20, for example 5, and m is an integer greater than about 10 and preferably less than 500, particularly less than 100, for example 30.

The novel compounds are illustrated in Examples 1, 3 and 7 below. They are useful in the Thiol/ene compositions of the invention.

In addition to the compounds described in the Examples below, other suitable styryloxy monomers include the following: 1. Reaction products of hydroxyl containing styryloxy compounds with:

a) Polyfunctional isocyanates.

- e.g. the urethane formed by reacting 2 equivalents of 4-(2-hydroxyethoxy)-3-methoxyprop-1-enylbenzene with 1 equivalent of diphenylmethane diisocyanate.

b) Polyfunctional carboxylic acids or acid chlorides.

e.g. the ester formed by reacting 2 equivalents of 4-(2-hydroxypropoxy)-3-prop-1-enylprop-1-enylbenzene with 1 equivalent of sebacoyl chloride.

c) Dianhydrides.

e.g. the ester formed by reacting 2 equivalents of 4-(2-hydroxyethoxy)prop-1-enylbenzene with 1 equivalent of pyromellitic dianhydride.

d) Aldehydes.

e.g. the acetal formed by reacting 2 equivalents of 4-(2-hydroxyethoxy)prop-1-enylbenzene with one equivalent of acrolein.

e) Polyepoxides.

e.g. the styryloxy substituted Novolac resin formed by reacting 2.7 equivalents of 4-(2-hydroxyethoxy)prop-1-enylbenzene with 1 equivalent of epoxy cresol Novolac Resin ECN 1235 (supplied by Ciba Geigy Corp.).

f) Polyfunctional esters.

e.g. the ester formed by reacting 2 equivalents of 4-(2-hydroxyethoxy)prop-1-enylbenzene with one equivalent of dimethylphthalate.

2. Reaction products of 3-hydroxy-4-alkoxystyrenes with a) Polyfunctional isocyanates.

e.g. the urethane formed by reacting 2 equivalents of 2-methoxy-5-prop-1-enylphenol with 1 equivalent of isophorone diisocyanate.

b) Dianhydrides.

e.g. the ester formed by reacting 2 equivalents of 2-methoxy-5-prop-1-enylphenol with 1 equivalent of 3,3',4,4'-benzophenone-tetracarboxylic dianhydride.

c) Polyepoxides.

e.g. the isocyanurate formed by reacting 3 equivalents of 2-methoxy-5-prop-1-enylphenol with 1 equivalent of triglycidyl ether isocyanurate.

d) Multifunctional acid chlorides.

e.g. the ester formed by reacting 2 equivalents of 2-methoxy-5-prop-1-enylphenol with 1 equivalent of terephthaloyl chloride.

The multifunctional thiol may be chosen from compounds having 2 or more mercapto groups (—SH) per molecule. Suitable polythiols are described in U.S. Pat. Nos. 3,661,744, 4,008,341 and 4,119,617 mentioned above. The polythiol component suitably has a molecular weight in the range from about 50 to about 20,000 and is of the general formula

R—(SH)$_9$ where R is a polyvalent organic moiety free from reactive carbon-to-carbon unsaturation and 9 is at least two.

The free radical curing rate accelerator may be of any of the known types of accelerator or polymerisation initiator which activate the composition photochemically, thermally or by chemical (Redox) action. Suitable photocuring rate accelerators are described in U.S. Pat. No. 3,661,744, particularly the aldyhyde and ketone carbonyl compounds having at least one aromatic nucleus attached directly to the

group.

Examples include benzophenone, acetophenone, 2,2-dimethoxy-2-phenylacetophenone and derivatives thereof. The rate accelerator may be suitably present over the range 0.05-10% by weight of the total weight of the composition.

Optionally the composition may contain an organic solvent (e.g. ethylacetate or 1,1,1-trichloroethane) and a free radical stabiliser or inhibitor to prevent premature onset of curing (e.g. hydroquinones, benzoquinones, naphthoquinones, phenanthraquinones and substituted compounds of any of the foregoing, or phenols such as 2,6-di-tert-butyl-4-methyl phenol).

Other optional ingredients of the composition include coinitiators or photosensitizers, thickeners, pigments, dyes, toughening agents, antioxidants, acids (e.g. phosphorous acid), wetting agents, flow control agents and adhesion promoters, all of which are of types known in the prior art.

The present invention provides novel thiol/ene compositions which are capable of more rapid curing than commercially available thiol/ene systems and which have good thermal resistance. They can be used for numerous applications which are known for thiol/ene compositions, such as coatings, potting compositions and sealing and gasketting materials.

DESCRIPTION OF THE PREFERRED EMBODIMENTS

The invention is illustrated in the following examples:

EXAMPLE 1

A mixture of isoeugenol (24.6 g), 3,4-epoxycyclohexylmethyl3,4-epoxycyclohexane carboxylate (18.75 g) (available under the trade name ERL-4221 from Union Carbide) and potassium hydroxide (0.09 g) was heated at 100° C. for 71 hours. After this time, thin layer chromatography (t.l.c.) indicated that the isoeugenol had been almost consumed. On cooling, a yellow solid was obtained. T.l.c. analysis of this material indicated the presence of many compounds and a mass spectrum showed the major component to be the difunctional styryloxy monomer (M$^+$at 580.4=12% [C$_{34}$H$_{44}$O$_8$]; (M-164)$^+$at 416.2=3% [C$_{24}$H$_{32}$O$_6$]; M/e=164.1 [C$_{10}$H$_{12}$O$_2$]) exemplified by the formula:

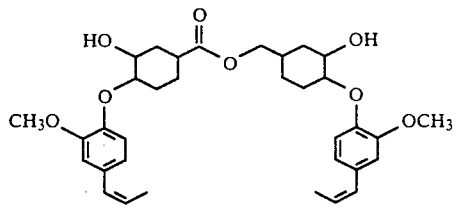

along with material isomeric to this structure. Gel permeation chromatography (G.P.C.) showed that 60% of the resin corresponded to the difunctional styryloxy resin, 25% to higher molecular weight analogues and polymer and 15% to lower molecular weight compounds including minor amounts of the starting phenol.

EXAMPLE 2

An ultra-violet (UV) light sensitive composition was prepared by heating to 80° C. a mixture of 1.45 g of the resin obtained in Example 1, 1.11 g of pentaerythrital tetrakis mercaptopropionate (mercaptate Q-43 ester supplied by Cincinnati Milacron Chemicals) and 2,2-dimethoxy-2-phenylacetophenone (0.08 g) until a homogeneous blend was obtained. A 100 micron thick coating of the blend was then prepared on a standard 1×4" microscope glass slide and the coating exposed to ultraviolet light from a medium pressure mecury arc lamp operating at 200 W/inch (Porta-Cure 1000, American Ultraviolet Co.).

After 5 seconds exposure, the coating had cured to a dry film which was found to be insoluble in acetone. The light intensity at the curing surface was measured using an International Light Co. light meter (model 1L-443) with 365 nm probe and found to be 60mW/cm².

EXAMPLE 3

Isoeugenol (16.47 g), allyl glycidyl ether )11.42 g) and Amberlyst A-21 (2.02 g) resin were heated together at 105° C. for 8 hours. After this time, t.l.c. analysis indicated that most of the starting isoeugenol had been consumed. The Amberlyst resin was separated from the reaction mixture and the remaining brown coloured liquid was analysed by G.P.C. The chromatogram showed only one peak corresponding to a higher molecular weight product than either of the starting compounds. This compound is believed to be the simple condensation product of the phenol and the epoxide and has the structure:

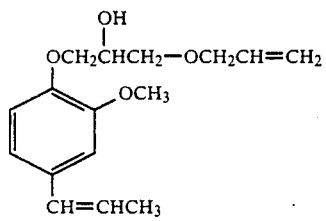

EXAMPLE 4

U.V. sensitive compositions were prepared by blending the following materials together (all parts by weight):

|  | Composition A | Composition B |
|---|---|---|
| Resin of Example 3 | 51.3 | 66.8 |
| Mercaptate Q43 | 45.0 | 29.3 |
| 2,2-dimethoxy-2-phenylacetophenone | 3.7 | 3.9 |

Coatings were prepared as described in Example 2. After 20 secs. exposure (UV conditions as Example 2), Composition A had cured to a tack-free film with good adhesion to the glass surface. Approximately 60 secs. exposure was required to cure Composition B which was softer than Composition A.

EXAMPLE 5

4-isopropenylphenol (8.9 g) [prepared by the method described by J. Kahovec et al, *Collection Czechoslov. Chem. Commun.*, Vol. 36, page 1986, (1970)], allylglycidyl ether (7.6 g) and Amberlyst A-21 resin (1.0 g) were heated together at 115° C. for 6.5 hours. After this time, t.l.c. analysis indicated that the starting phenol had been almost consumed. Removal of the Amberlyst resin gave a brown coloured liquid believed to be the condensation product of the starting phenol and epoxide, represented by the formula:

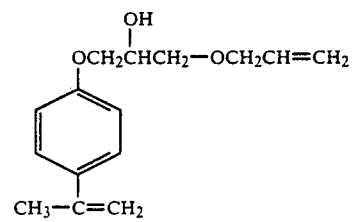

EXAMPLE 6

UV sensitive compositions were prepared by blending the following materials together (wt. in grams):

|  | Composition C | Composition D |
|---|---|---|
| Reaction product of Example 5 | 6.2 | 6.2 |
| Mercaptate Ester, Q43 | 6.1 | 3.0 |
| 2,2-dimethoxy-2-phenylacetophenone | 0.5 | 0.4 |

Coatings of these compositions were prepared as described in Example 2. After 50 secs. exposure to UV light (conditions as described in Example 2), cured tack free films were obtained. Composition D was harder than Composition C.

EXAMPLE 7

12.59 of a heptafunctional epoxidised polydimethylsiloxane of approximate molecular weight 3,380 (prepared by a hydrosilation reaction of one equivalent of the corresponding heptafunctional hydro siloxane and seven equivalents of allyl glycidyl ether in the presence of a platinum catalyst), 2.22 g of isoeugenol and 1.38 grams of Amberlyst Resin A-21 were heated together at 110° C. for 17 hours. After this time, t.l.c. analysis indicated that all of the isoeugenol was consumed. The infra red (I.R.) spectrum of the reaction mixture showed a peak at 3480 cm$^{-1}$ due to the presence of an hydroxyl group. The Amberlyst resin was separated from the reaction mixture to yield a product predominately of the formula:

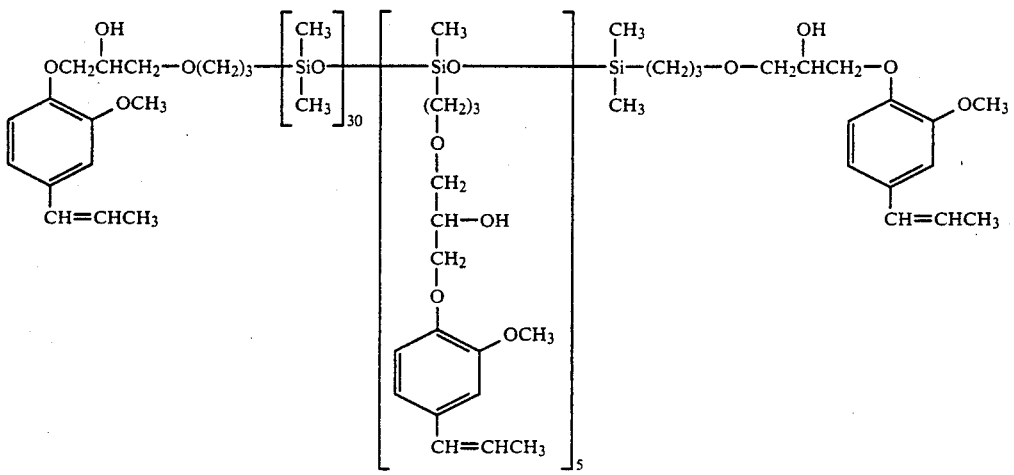

A mixture was prepared by blending 8.4 g of this resin with 1.2 g of mercaptate ester Q43 and 0.4 g of 2,2-dimethoxy-2-phenylacetophenone. A coating of the material was prepared as described in Example 2 and exposed to UV light from a Technocure 200 W/IN mercury lamp at an intensity of 50mW/cm² (365nm) for 30 secs. After this time, a dry to touch, soft, cured film was obtained.

EXAMPLE 8

To a solution of 122 g 4-hydroxybenzaldehyde in 500 mls acetone was added 276 g potassium carbonate. This mixture was stirred for 15 minutes. A solution of 133 g allyl bromide in 200 mls acetone was then added dropwise over 30 minutes. The resulting mixture was heated at reflux for 1 hour, left standing for a further 16 hours and finally heated at reflux for 2 hours. After filtration, the solvent was removed by distillation leaving 175 g of a reddish liquid. This residue was distilled under reduced pressure (B.Pt. 104°-114° C. at 1.5 mmHg) to yield 130 g of a pale yellow liquid which was identified by infrared and n.m.r. spectroscopy as 4-allyloxybenzaldehyde.

To a solution of 9.36 g potassium metal in 500 mls tert-butanol was added 85.68 g methyltriphenylphosphonium bromide. The resulting yellow suspension was stirred for 20 minutes and 32.4 g 4-allyloxybenzaldehyde was then added over 10 minutes. This mixture was stirred for 30 minutes and then allowed to stand overnight. After filtration the solvent was removed under reduced pressure leaving 107 g of a red semi-solid residue. Petroleum ether (B.Pt. 40°-60° C.) was added to the residue precipitating a solid which was filtered. After removal of the petroleum ether, the remaining resin was distilled under reduced pressure (B.Pt. 68°-82° C. at 0.4 mmHg) yielding 26.7 g of a clear colorless liquid which was identified by infrared and n.m.r. spectroscopy as 4-allyloxystyrene (Proton NMR: (CDCl$_3$)$\delta$=4.50, 4.58, doublet, allyloxymethylene protons; $\delta$=5.0-6.5, multiplets, allyl and vinyl group protons;$\delta$=6.80, 6.95, 7.30 and 7.45, quartet, aromatic protons).

EXAMPLE 9

UV sensitive compositions based on 4-allyloxystyrene (prepared as in Example 8) were formulated (quantities are all parts by weight):

|  | Composition E | Composition F | Composition G |
| --- | --- | --- | --- |
| 4-allyloxystyrene | 13.0 | 13.0 | 8.0 |
| Mercaptate ester, Q43 | 12.2 | 12.2 | 12.2 |
| 2,2,-dimethoxy-2-phenyl-acetophenonone | — | 1.3 | 1.3 |
| 2,2-diethoxyacetophenone | 1.3 | — | — |
| 4-methyl-2,6-di-t-butylphenol | 0.1 | 0.1 | 0.1 |

A one mm thick coating of each of these compositions was prepared on a 1×4" microscope glass slide and exposed to UV light from a UVA LOC 1000W mercury lamp (Trade Mark Loctite Corp.) operating at 200W per inch. Compositions E and F gave a cured tack-free film after 30 secs. exposure. Composition G was cured tack-free after 10 secs. exposure. All of these coatings were insoluble in dichloromethane. Composition G gave a tougher coating than either E or F. In each case, the coating was located 14 cms directly under the mercury arc. The light intensity at this point was measured using an Optical Associates Inc., light meter (model 206) with a 365 nm probe and found to be 150 mW/cm².

EXAMPLE 10

4-allyloxy-3-methoxystyrene was prepared from vanillin by a method analogous to that described in Example 8. In this case, the intermediate product 4-allyloxy-3-methoxybenzaldehyde was obtained by vacuum distillation at 152-158° C. and 7 mbar in 83% yield and the styryloxy derivative at 92-110° C. and 0.5 mbar in 58% yield.

A UV sensitive composition was prepared by blending 9.5 g 4-allyloxy-3-methoxystyrene, 12.2 g of mercaptate ester Q43, 0.9g 2,2-dimethoxy-2-phenylacetophenone and 0.1 g 4-methyl-2,6-di-t-butylphenol. A coating of the composition was prepared and irradiated as described in Example 9. In this case, a tack-free, cured film was obtained after 15 secs.

EXAMPLE 11

To a solution of !36g 4-hydroxyacetophenone in 500 mls acetone was added 276.41 g potassium carbonate. This mixture was stirred for 15 minutes. A solution of 133 g allyl bromide in 200 mls acetone was then added dropwise over 45 minutes, and the resulting mixture was stirred for a further 4 hours and left standing for a further 16 hours. Thin-layer chromatography showed some starting material to be present at the end of this time. The mixture was then heated to reflux for 4 hours and left standing a further 16 hours. After this time the solvent was removed by distillation leaving 230 g of a brown liquid. This residue was distilled under reduced pressure (B.Pt. 107–115° C. at 0.6 mmHg.) to yield 158 g of pale yellow liquid which was identified by infrared and n.m.r. spectroscopy as 4-allyloxyacetophenope.

To a solution of 5.58 g potassium metal tert-butanol was added 51 g methyl triphenylphosphonium bromide. The resulting yellow suspension was stirred for 20 minutes. A solution of 18.86 g 4-allyloxyacetophenone in 30 mls tert-butanol was then added gradually and stirred for 16 hours at room temperature. After this time, the mixture was filtered and solvent removed under reduced pressure. The resulting mixture was extracted with petroleum ether to yield 28 g of brown resin. This resin was distilled under reduced pressure (B.Pt. 88° C. at 1mm Hg) yielding 15.21 g of a clear colorless liquid which was identified by infrared and n.m.r. spectroscopy as 4-allyloxy isopropenyl benzene (Proton NMR: $(CDCl_3)\delta=2.12$ singlet, α-methyl protons;$\delta=4.50$, 4.58, doublet, allyloxy methylene protons;$\delta=5.0-6.5$, multiplets, allyl and vinyl group protons;$\delta=6.80, 6.95, 7.35$ and $7.50$, quartet, aromatic protons).

A UV sensitive composition was prepared by blending 8.7 g of this material, 12.2 g of mercaptate ester Q43 and 0.8 g 2,2-dimethoxy-2-phenylacetophenone. A 0.25 mm thick coating was prepared and irradiated with UV light as described in Example 9. A tack-free cured film was obtained after 30 secs. exposure.

EXAMPLE 12

4-allyloxy-3-methoxypropenylbenzene was prepared by refluxing a stirred mixture of isoeugenol (164 g),allybromide (133 g) and potassium carbonate (278 g) in dry acetone (700 mls) for 18 hours. Removal of the solids and solvent gave a crude product 208 g which was vacuum distilled to yield 130 g of pure 4-allyloxy-3-methoxy-prop-1-enylbenzene (b.p.. 104–118° C. at 0.1 imbar).

A UV sensitive composition was prepared by blending 10.3 g of this material with 12.2 g of mercaptate ester Q43 and 0.9 g 2,2-dimethoxy-2-phenylacetophenone. A coating (0.25 mm thick) was prepared and irradiated under UV light (as detailed in Example 9). A tack-free cured film was obtained after 10 secs. exposure.

EXAMPLE 13

Isovanillin (76 g) was dissolved in a stirred mixture of potassium carbonate (104 g) and acetone (450 mls) followed by the dropwise addition of allyl bromide (67 g) over ca. 20 mins. The mixture was refluxed for 5 hours, cooled and filtered. The solvent was removed from the filtrate under reduced pressure and the residue was distilled under vacuum to yield 3-allyloxy-4-methoxybenzaldehyde (85 g), b.p. 137–150° C. at 1.5 mbar.

60MHz, $^1$HMR, $(CDCl_3)\tau0.2(s, IH, CHO)$, $\tau2.45-3.1$ (m,3H, ArH), $\tau3.6-4.9$ (m, 3H, $CH=CH_2$), $\tau5.35$, (d, 2H, $OCH_2$), $\tau6.1$ (S, 3H, $OCH_3$)

Sodium amide (39 g) was dispersed in dry tetrahydrofuran (800 Dmls). Methyltriphenylphosphonium bromide (102 g) was added and the mixture stirred at R.T. for 2 hours. 3-allyloxy-4-methoxy-benzaldehyde (50 g) was then added dropwise over ca. 15 mins. and the mixture stirred for a further 3 hours. The mixture was filtered and the solvent removed from the filtrate under reduced pressure. The residue was washed with diethyl ether (1.51) and the solvent removed to yield a brown coloured resin. The washing process was repeated and the residue obtained was distilled under reduced pressure to give 3-allyloxy-4-methoxystyrene (29.5 g), b.p.98–104° C. at 0.8 mbar.

60MHz, $^1$HMR $(CDCl_3)\tau2.45-4.90$ (m, 9H, ArH+vinyl $CH=CH_2$+allyl $CH=CH_2$), $\tau5.35$ (d, 2H, $OCH_2$), $\tau6.1$ (S, 3H, $OCH_3$).

A UV sensitive composition was prepared by blending 9.5 g of this material with 12.2 g of mercaptate ester Q43 and 0.9 g 2,2-dimethoxy-2-phenylacetophenone 0.5 mm thick coatings were prepared and irradiated with UV light as described in Example 9. After 10 secs. exposure, a tack-free cured film had formed.

EXAMPLE 14

Isoeugenol (16.46 g), 1,4-dibromobutane (11.88 g) and tetra-n-butylammonium bromide (3.22 g) were added to a stirred suspension of potassium carbonate (20.7 g) in dry toluene (100 g). The mixture was heated at 105° C. for 20 hrs. After this time t.l.c. analysis indicated that all of the starting isoeugenol had been consumed. The mixture was filtered and the toluene solution washed with water (3×100 mls). After drying (sodium sulphate), the toluene was removed under reduced pressure to yield 14.25 g of a white solid. The solid was recrystallised from a mixture of ethanol and chloroform to give 4.94 g of a pure product of the structure:

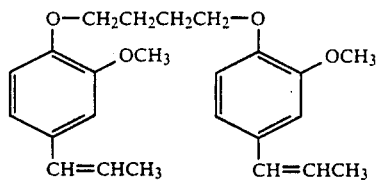

The m.p. was 135° C. The infra red spectrum showed no phenolic hydroxyl group, indicating that the pure dialkylated product had been isolated.

A UV sensitive composition was prepared by blending together a hot mixture of 1.9 g of this material with 20.4 g of 4-allyloxy-3-methoxy-1-propenyl benzene as prepared in Example 12. On cooling, 25.4 g of mercaptate ester Q43 and 0.23 g of 2,2-diethoxyacetophenone were added. 0.25 mm thick coatings of the composition were prepared and irradiated as detailed in Example 9. After 30 secs. exposure, a tack-free cured film was obtained.

EXAMPLE 15

O-propenylphenol (67 g) was added to a stirred suspension of potassium carbonate (138 g) in dry acetone. Allyl bromide (67 g) was then added dropwise over about 20 minutes and the stirred mixture was heated under reflux for 4 hours. After this time, gas liquid chromatography indicated that the phenol had been converted to about 95% of a mixture of cis and trans 2-allyloxy-1-propenylbenzene. The mixture was filtered and the solvent removed under reduced pressure. The residue was vacuum distilled and yielded 58.9 g of almost pure 2-allyloxy-1-propenylbenzene which was identified spectroscopically. [b.p. 64–88° C. at 0.6 mbar].

60MHz, 'HMR (CDCl$_3$) : 2.6–5.0, 9H, multiplets due to AR—H, —CH=CH$_2$ and —CH=CH—; 5.5, doublet, 2H, O—CH$_2$—; 8.2, doublet 3H, —CH$_3$ A UV sensitive composition was prepared by blending 8.7 g of this styryloxy resin with 12.2 g of mercaptate ester Q43 and 0.8 g of 2,2-dimethoxy-2-phenylacetophenone. A 0.25 mm thick coating was prepared and irradiated as in Example 9. In this case, a tack free surface sure was obtained after 10 seconds irradiation.

We claim:

1. Curable compositions comprising
   1) a multifunctional styryloxy monomer having one or more of the following structures

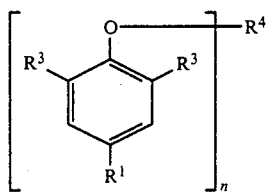

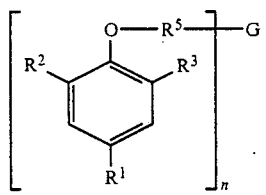

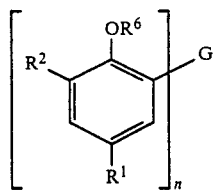

wherein

R$^1$, R$^2$ and R$^3$ are selected from vinyl (—CH=CH$_2$), 1-propenyl(—CH=CH—CH$_3$), isopropenyl

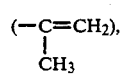

hydrogen, lower alkyl or alkoxy, provided that at least one of R$^1$, R$^2$ and R$^3$ must be vinyl, 1-propenyl or isopropenyl;

n is an integer ≧ 1;

if n=1, then R$^4$ is a monovalent hydrocarbon radical containing one free-radically copolymerisable alkenyl or cycloalkenyl group, if n≧2, R$^4$ is a multivalent hydrocarbon radical which may contain a maximum of one free-radically copolymerisable alkenyl or cycloalkenyl group;

R$^5$ is a divalent hydrocarbon radical; or a carbon atom which is part of a cyclic group in the radical G; or a radical of formula

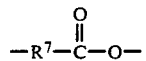

where R$^7$ is a divalent hydrocarbon radical;

if n=1, G is a monovalent organic or inorganic radical, free of phenolic hydroxyl groups or other groups which substantially interfere with radical polymerisation, containing one free-radically copolymerisable alkenyl or cycloalkenyl group;

if n≧2, G is a multivalent organic or inorganic radical, free of phenolic hydroxyl groups or other groups which substantially interfere with radical polymerisation, which may contain a maximum of one free-radically copolymerisable alkenyl or cycloalkenyl group;

R$^6$ is a lower alkyl or cycloakyl group; or if n=1, R$^6$ may also be an alkenyl or cycloalkenyl group, provided that G does not contain an alkenyl or cycloalkenyl group.

2) a multifunctional thiol.

3) a free-radical curing rate accelerator.

2. A composition according to claim 1 wherein the mole ratio of styryloxy/thiol groups is from about 0.2/1 to about 5/1.

3. A composition according to claim 1 wherein the curing rate accelerator is present in an amount of 0.05–10% by weight of the total weight of the composition.

4. A composition according to claim 1 wherein R$^4$ is an alkenyl group.

5. A composition according to claim 4 wherein R$^4$ is an allylic group.

6. A composition according to claim 1 wherein when n=1, G is a straight or branched monovalent hydrocarbon radical which contains one free radially copolymerizable alkenyl group and which is unsubstituted or is substituted with a member of the group consisting of ether oxygen atoms and hydoxyl groups.

7. A composition according to claim 6 wherein G is an allyl alkyl ether group or a hydroxyl substituted allyl alkyl ether group.

8. A composition according to claim 1 wherein the multifunctional styryloxy monomer is selected from the group consisting of:

Reaction products of hydroxyl containing styryloxy compounds with
   (a) Polyfunctional isocyanates,
   (b) Polyfunctional carboxylic acids or acid chlorides,
   (c) Dianhydrides,
   (d) Aldehydes,
   (e) Polyepoxides,
   (f) Polyfunctional.

9. A composition according to claim 1 wherein the free-radical curing rate accelerator is a photoinitiator.

10. A composition according to claim 9 wherein the free-radical photoinitiator comprises an aldehyde or ketone carbonyl compound having at least one aromatic nucleus attached directly to the —C(O)—group.

* * * * *

UNITED STATES PATENT AND TRADEMARK OFFICE
CERTIFICATE OF CORRECTION

PATENT NO. : 5,021,512

DATED : June 4, 1991

INVENTOR(S) : Woods et al

It is certified that error appears in the above-identified patent and that said Letters Patent is hereby corrected as shown below:

In the Abstract:
　　In the second column of page 1, in the formula:

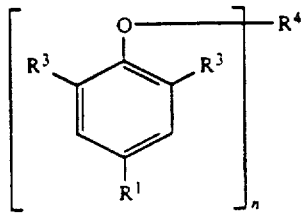

should be

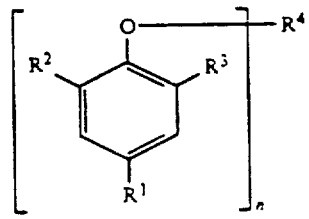

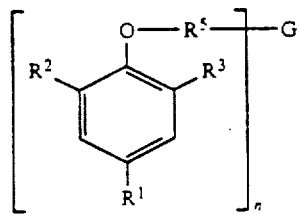

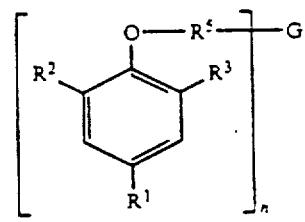

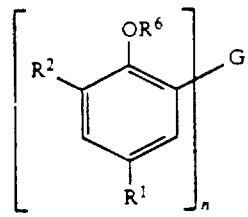

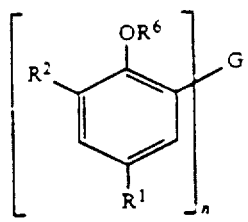

Col. 1, lines 42-43, "polyaryoxyphosphazene" should be corrected to
　　--polyaryloxyphosphazene--.

UNITED STATES PATENT AND TRADEMARK OFFICE
CERTIFICATE OF CORRECTION

PATENT NO. : 5,021,512

DATED : June 4, 1991

INVENTOR(S) : WOODS ET AL

It is certified that error appears in the above-identified patent and that said Letters Patent is hereby corrected as shown below:

Col. 2, lines 25-31, the first section of the formula,

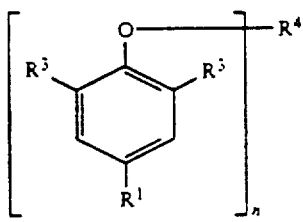   should be   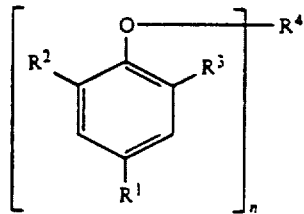

Col. 2, line 60, delete the exclamation point (!) before "lower".

Col. 5, line 41, the formula should be corrected from

"R—(SH)$_9$"   to   -- R—(SH)$_q$ --.

Col. 5, line 44, "9" should be changed to correctly read --q--.

Col. 6, line 23, "ylmethyl3,4-epoxycyclohexane" should be corrected to read -- ylmethyl-3,4-epoxycyclohexane --

Col. 8, line 49, change "12.59" to correctly read --12.5 g--.

Col. 11, line 10, change "4-allyloxyacetophenope" to correctly read -- 4-allyloxyacetophonone --.

Col. 11, line 43, change "imbar)" to correctly read -- mbar) --.

Col. 11, line 65, change "(800 Dmls)" to correctly read --(800mls)--.

UNITED STATES PATENT AND TRADEMARK OFFICE
CERTIFICATE OF CORRECTION

PATENT NO. : 5,021,512
DATED : June 4, 1991
INVENTOR(S) : Woods et al

It is certified that error appears in the above-identified patent and that said Letters Patent is hereby corrected as shown below:

In the Claims:

Col. 13, lines 20-45, the formula should be changed as follows:

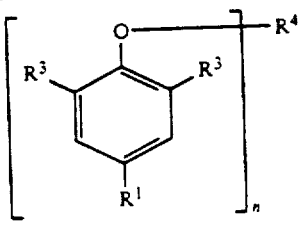

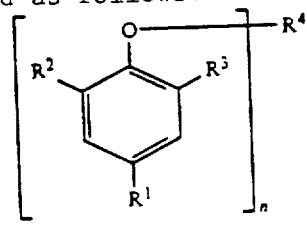

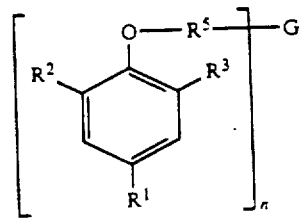

should correctly read

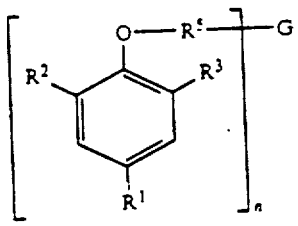

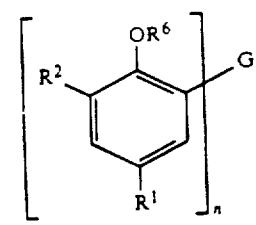

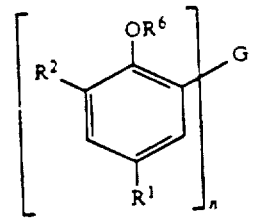

Col. 14, line 59, --esters.-- should be inserted after "Polyfunctional".

UNITED STATES PATENT AND TRADEMARK OFFICE
CERTIFICATE OF CORRECTION

PATENT NO. : 5,021,512
DATED : June 4, 1991
INVENTOR(S) : Woods et al

It is certified that error appears in the above—identified patent and that said Letters Patent is hereby corrected as shown below:

Col. 14, line 22, change "cycloakyl" to correctly read --cycloalkyl"

Signed and Sealed this

Twenty-second Day of December, 1992

Attest:

DOUGLAS B. COMER

Attesting Officer

Acting Commissioner of Patents and Trademarks